(12) United States Patent
Beernink et al.

(10) Patent No.: US 7,585,815 B2
(45) Date of Patent: Sep. 8, 2009

(54) HIGH THROUGHPUT PROTEIN PRODUCTION SCREENING

(75) Inventors: Peter T. Beernink, Walnut Creek, CA (US); Matthew A. Coleman, Oakland, CA (US); Brent W. Segelke, San Ramon, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 10/884,783

(22) Filed: Jul. 1, 2004

(65) Prior Publication Data

US 2005/0019807 A1 Jan. 27, 2005

Related U.S. Application Data

(60) Provisional application No. 60/490,099, filed on Jul. 24, 2003.

(51) Int. Cl.
*C40B 20/02* (2006.01)
*C40B 20/04* (2006.01)
*A23J 16/00* (2006.01)
*C12Q 1/68* (2006.01)
*C12P 21/06* (2006.01)

(52) U.S. Cl. ............... 506/3; 506/4; 435/6; 435/68.1; 530/412

(58) Field of Classification Search ............ 506/3, 506/4; 435/6, 68.1; 530/412
See application file for complete search history.

(56) References Cited

U.S. PATENT DOCUMENTS

| | | | |
|---|---|---|---|
| 5,616,478 A * | 4/1997 | Chetverin et al. | 435/91.2 |
| 5,643,768 A * | 7/1997 | Kawasaki | 435/91.21 |
| 5,658,754 A * | 8/1997 | Kawasaki | 435/69.1 |
| 6,274,321 B1 | 8/2001 | Blumberg | 435/6 |
| 6,303,337 B1 * | 10/2001 | Rothschild et al. | 435/69.1 |
| 6,306,628 B1 * | 10/2001 | Rothschild et al. | 435/91.3 |
| 6,448,033 B1 * | 9/2002 | Kudlicki et al. | 435/69.1 |
| 6,800,453 B2 * | 10/2004 | Labaer et al. | 435/68.1 |
| 6,927,025 B1 * | 8/2005 | Carr et al. | 435/6 |

OTHER PUBLICATIONS

Beernink PT et al, Protein Society Aug. 2002; "In Vitro Protein Expression Screening for Human Proteomics".
Coleman MA et al, (2004) "High-throughput, fluorescence-based screening for soluble protein expression." J Proteome Res. Sep.-Oct.; 3(5):1024-32.
Beernink et al (2003) "Application of cell-free expression systems to proteomic studies." in Cell Free Protein Expression, James R. Swartz (Ed.) Springer Verlag.
Beernink et al (2002) "Application of in vitro protein expression to human proteomics." Miami Winter Symposium Jan. 2002. (abstract/poster mentioned in ROI).
Pedelacq JD, Piltch E, Liong EC, Berendzen J, Kim CY, Rho BS, Park MS, Terwilliger TC, Waldo GS (2002) Engineering soluble proteins for structural genomics. Nat Biotechnol 20: 927-932.
Yokoyama S (2003) Protein expression systems for structural genomics and proteomics. Curr Opin Chem Biol 7: 39-43.
Fields S, Song O (1989) A novel genetic system to detect protein interaction. Nature 340: 245-246.
Schweitzer B, Kingsmore SF (2002) Measuring proteins on microarrays. Curr Opin Biotechnol 13: 14-19.
Pawlak M, Schick E, Bopp MA, Schneider MJ, Oroszlan P, Ehrat M (2002) Zeptosens' protein microarrays: a novel high-performance microarray platform for low abundance protein analysis. Proteomics 2: 383-393.
Haab BB, Dunham MJ, Brown PO (2001) Protein microarrays for highly parallel detection and quantitation of specific proteins and antibodies in complex solutions. Genome Biol 2:research0004.1-0004.13.
Kononen J, Bubrndorf L, Kallioniemi A et al. (1998) Tissue microarrays for high throughput molecular profiling of tumor specimens. Nature Medicine 4: 844-847.
Huang RP (2001) Detection of multiple proteins in an antibody-based protein microarray system. J Immunol Methods 255: 1-13.
Wiese R, Belosludtsev Y, Powdrill T, Thompson P, Hogan M (2001) Simultaneous multianalyte ELISA performed on a microarray platform. Clinical Chem 47: 1451-1457.
Waldo GS, Standish BM, Berendzen J, Terwilliger TC (1999) Rapid protein-folding assay using green fluorescent protein. Nat Biotechnol 17: 691-695.
Bussow K, Nordhoff E, Lubbert C, Lehrach H, Walter G (2000) A human cDNA library for high-throughput protein expression screening. Genomics 65: 1-8.
Martin GA, Kawaguchi R., Lam Y, DeGiovanni A, Fukushima M, Mutter W (2001) High-yield, in vitro protein expression using a continuous-exchange, coupled transcription/translation system. BioTechniques 31: 948-953.
Hammarstrom M, Hellgren N, van Den Berg S, Berglund H, Hard T (2002) Rapid screening for improved solubility of small human proteins produced as fusion proteins in *Escherichia coli*. Protein Sci 11: 313-321.

(Continued)

*Primary Examiner*—Amber D. Steele
(74) *Attorney, Agent, or Firm*—John H. Lee

(57) ABSTRACT

Methods, compositions, and kits for the cell-free production and analysis of proteins are provided. The invention allows for the production of proteins from prokaryotic sequences or eukaryotic sequences, including human cDNAs using PCR and IVT methods and detecting the proteins through fluorescence or immunoblot techniques. This invention can be used to identify optimized PCR and WT conditions, codon usages and mutations. The methods are readily automated and can be used for high throughput analysis of protein expression levels, interactions, and functional states.

17 Claims, 2 Drawing Sheets
(2 of 2 Drawing Sheet(s) Filed in Color)

OTHER PUBLICATIONS

Coleman MA, Eisen JA, Mohrenweiser HW (2000) Cloning and characterization of HARP/SMARCAL1: a prokaryotic HepA-related SNF2 helicase protein from human and mouse. Genomics 65: 274-282.

Doyle SA, Murphy MB, Massi JM, Richardson PM (2002) High-throughput proteomics: a flexible and efficient pipeline for protein production. J Proteome Res 1: 531-53.

* cited by examiner

SEQUENCE LISTING

<160> NUMBER OF SEQ ID NOS: 3

<210> SEQ ID NO 1
<211> LENGTH: 36
<212> TYPE: DNA

-continued

```
<213> ORGANISM: Artificial Sequence
<220> FEATURE:
<223> OTHER INFORMATION: Description of Artificial Sequence: Synthetic
      primer

<400> SEQUENCE: 1
gcgcgcgaga tctcgatccc gcgaaattaa tacgac                                36

<210> SEQ ID NO 2
<211> LENGTH: 33
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
gcgcgcgtat ccggatatag ttcctcctttt cag                                  33

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence: Synthetic
      6X-His tag

<400> SEQUENCE: 3

His His His His His His
 1               5
```

HIGH THROUGHPUT PROTEIN PRODUCTION SCREENING

CLAIM OF PRIORITY IN PROVISIONAL APPLICATION

This application claims the benefit of U.S. Provisional Application No. 60/490,099 filed Jul. 24, 2003.

The United States Government has rights in this invention pursuant to Contract No. W-7405-ENG-48 between the United States Department of Energy and the University of California for the operation of Lawrence Livermore National Laboratory.

BACKGROUND OF THE INVENTION

1. Field of the Invention

The invention relates to methods and compositions for in vitro protein expression, and more particularly to high throughput methods and compositions for analyzing protein expression and protein interactions.

2. Description of the Related Art

In vitro transcription and translation methods are known in the art and have historically been used to produce proteins that may be difficult to produce in vivo for one or more reasons. In vitro translation systems are known in the art and are available for purchase from Promega as the TNT Quick Coupled Transcription/Translation System or from Roche Diagnostic Corporation as the Rapid Translation System (RTS). Amino acyl tRNAs including a fluorescently-labeled amino acyl moiety also are known in the art as is their use in vitro translation. One such labeling system is available from Promega as the FluoroTect Protein Labeling System. While these systems provide facile production and labeling of proteins in vitro, they suffer from the difficulty that time-consuming separation techniques such as, e.g., gel electrophoresis are used to separate incorporated from unincorporated label following the in vitro translation reaction prior to analyzing protein expression. This slows overall throughput and increases the cost associated with the in vitro translation process and limits its utility in high throughput applications for, e.g., studying protein interactions. Thus, there is need in the art for high throughput methods, compositions and kits for carrying out in vitro translation and downstream analyses of in vitro translated reaction products. The invention provides for these and other advantages as described in detail below. Nothing in this section is to be construed as an admission that the described art is prior art to the instant invention.

SUMMARY OF THE INVENTION

The present invention is defined by the following claims, and nothing in this section should be taken as a limitation on those claims. Disclosed herein are methods, compositions and kits for carrying out in vitro translation reactions and for analyzing in vitro translated reaction products.

Accordingly, in one aspect, the invention provides a method for parallel analysis of a plurality of protein expression levels the method comprising carrying out in a plurality of separate reaction mixtures in vitro translation reactions in the presence of an aminoacyl tRNA, said amino acyl tRNA comprising a label on the amino acid moiety of said amino acyl tRNA to generate a plurality of labeled reaction products, spotting said plurality of labeled reaction products onto a substrate, and detecting said plurality of labeled reaction products.

In another aspect, the invention provides a method of parallel analysis of protein interactions, the method comprising carrying out in a plurality of separate reaction mixtures in vitro translation reactions, spotting the reaction mixtures onto a substrate, exposing the substrate to a test compound, and determining whether said test compound binds to an in vitro translated reaction product present in said reaction mixtures. In preferred embodiments the test compound is a protein, a nucleic acid, or a small molecule.

In a variation of the invention, the in vitro translation reaction is preceded by an in vitro transcription reaction. In another variation, the in vitro transcription reaction uses as a template the product of a nucleic acid amplification reaction. In a preferred embodiment, the nucleic acid amplification reaction is a polymerase chain reaction (PCR), such as, e.g., a reverse-transcribed polymerase chain reaction (RTPCR). In another preferred embodiment, the one or more of the method steps of the invention are automated.

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee. These and other features, aspects, and advantages of the present invention will become better understood with regard to the following description, and accompanying drawings, where:

FIG. 1A is a BODIPY-labeled dot-blot of 48 clones, in duplicate (columns 1-6 and 7-12), imaged with a FluorImager 595 (Molecular Devices). Twofold serial dilutions of a HIS6-GFP control reaction are shown in the top strip. FIG. 1B is quantification reported as relative fluorescence units (RFU) from the blot shown in FIG. 1A. FIG. 1C is an immunoblot of the same membrane using an affinity tag-specific antibody. FIG. 1D is an image of an SDS PAGE of selected reactions from the same experiment. Lane 1 shows mass standards (at left, kDa); lane 2 is purified GFP (3 µg); lane 3 is A7 (pIVEX-GFP); lane 4 is A8 (no DNA template); lane 5 is B7; lane 6 is C7; lane 7 is G8; lane 8 is A9; lane 9 is B9.

FIG. 2A shows an array of purified GFP on a glass slide (CMT-GAPS, Corning). FIG. 2B shows IVT-expressed GFP fusion proteins and DNA controls arrayed on a glass slide: Row: 1 LcrH; 2 GFP; 3 XRCC1; 4 LcrG; 5 IVT extract; 6 DNA; 7 SFN5; 8 DNA. FIG. 2C shows array-based immunoassays to detect GFP fusion proteins; top row: fluorescence of IVT-produced GFP fusions; bottom row: GFP fusion protein detection using an anti-GFP primary antibody (BD Clontech) and a rhodamine-conjugated secondary antibody. FIG. 2D illustrates the protein SMARCAL1 associating primarily with nucleosomes (squares) and only weakly with individual histones (circles) and a RAD51-paralog interacting with free histones (circles) but not nucleosomes (squares).

DETAILED DESCRIPTION OF THE INVENTION

Advantages and Utility

Figure 1:
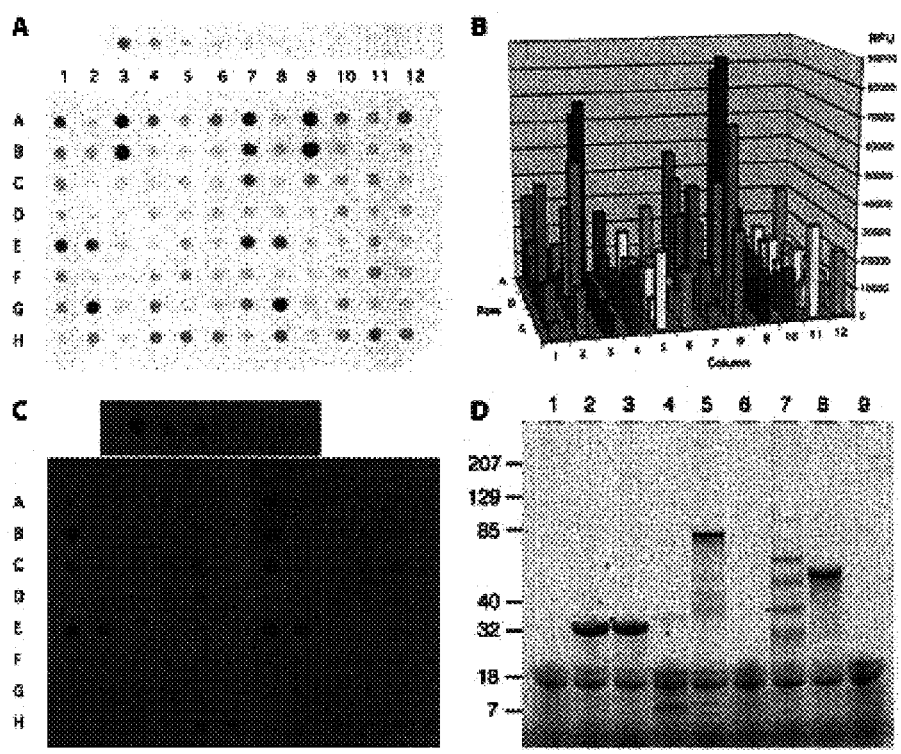
FIG. 1 depicts a cell-free protein expression array dot-blot and associated analyses of the reaction products.

Briefly, and as described in more detail below, described herein are high throughput, automatable methods and associated compositions and kits for production and analysis of in vitro expressed proteins.

Several features of the current approach should be noted. The invention can be practiced using small amounts of starting material such as, e.g., nanograms of any protein encoding nucleic acid as a template for protein production.

Advantages of this approach are numerous. They include reduced analytical, reagent, and labor costs, and increased throughput to speed the pace of discovery.

The invention is useful for analyzing protein expression levels in various cell types, various conditions (such as, e.g., prior to and following exposure to a test compound such as, e.g., a drug) and disease states, and for analyzing protein interactions with other proteins, nucleic acids, or test compounds.

Definitions

Terms used in the claims and specification are defined as set forth below unless otherwise specified. Method steps recited in the claims need not necessarily be performed in the recited order unless the language or context dictates otherwise.

The term "spotting" indicates that at least a portion of a reaction mix is transferred to a substrate for analysis carried out without use of a separation step that provides information about the molecular weight of a reaction product within the spotted mix.

It must be noted that, as used in the specification and the appended claims, the singular forms "a," "an" and "the" include plural referents unless the context clearly dictates otherwise.

Introduction

The promise of proteomics is to identify and characterize physical and functional properties of proteins and protein complexes simultaneously. Proteomics efforts require production of large numbers of purified proteins for biochemical or physical analyses. In particular, structural proteomics requires milligram quantities of highly purified proteins. Production of soluble protein (cf. denatured, aggregated and or otherwise insoluble protein) is a bottleneck in structural proteomics processes [1]. Many proteins are inherently poorly expressed, insoluble, cytotoxic or subject to proteolysis, which results in low, soluble expression in vivo. Cell-free protein expression strategies can overcome some of these problems and yield a larger number of expressed proteins [2]. Cell-free expression (also known as in vitro translation or "IVT") can also be used to identify rapidly well-expressed proteins and to obtain proteins for a variety of uses and studies.

The speed of IVT expression is especially useful when modest quantities of protein are needed, for example in enzyme assays or microarray studies. Microarray-based methods represent a high-throughput approach to identify and characterize specific protein interactions. Microarrays are an alternative to the yeast two-hybrid screen [3], which is highly sensitive, but can give false results for misfolded or transactivating proteins. In addition, protein arrays can identify other interactions, such as those with DNA and small molecules, interactions that potentially are useful for understanding the function of unannotated proteins [4, 5]. Protein arrays allow multiplexed protein detection along with sensitive quantification in a dense format [6, 7]. Protein arrays also hold potential for miniaturization and portability and therefore have broad applications in basic research, genomic annotation, identification of disease markers and diagnosis of disease [7, 8, 9].

METHODS OF THE INVENTION

The methods of the invention have a number of distinct advantages over existing technology. First, the methods are fast, requiring no bacterial growth or subcloning. Second, some proteins, such as cytotoxic or proteolytically sensitive proteins, can be expressed using IVT at levels sufficient for their detection and/or analysis using the methods of the invention, but are expressed at insufficient levels using in vivo expression systems such as E. coli. The methods of the invention can be practiced using T7-based clones using in vitro transcription and translation methods well known to the ordinarily skilled practitioner, or with non-T7 based clones using a two-step PCR procedure to incorporate the necessary T7 regulatory elements. This capability is conveniently available using the Linear Template Generation Set available from Roche Applied Science. Because the methods involve no living cells, they are applicable to proteins from disease-causing microorganisms or other bioterrorism agents.

Different and complementary detection systems can be used with the methods of the invention, including, e.g., immunoblotting based on an affinity tag (such as, e.g., a HIS tag), optionally incorporated during an amplification step such as, e.g., a PCR step, as known to ordinarily skilled practitioners, detection based on incorporation of a label such as a fluorescent label such as, e.g., a BODIPY-conjugated amino acid, optionally incorporated during an in vitro translation step. The use of a label provides for rapid detection but may in some instances affect protein conformation and function. Detection of unlabeled proteins through the use of an affinity tag therefore may be preferred if the resulting protein is to be used for a functional assay such as, e.g., a binding assay.

It has surprisingly been discovered that unincorporated label can be separated from in vitro translated reaction products by spotting the reaction products on a substrate such as a membrane (including, e.g., PVDF—trade name Immobilon, nylon, or nitrocellulose) or glass that preferably has been coated with a charged chemical agent such as, e.g., poly-L-lysine or gamma aminopropyl silane ("GAPS"). Thus, spotting the reaction product onto the substrate and washing the substrate effectively produces a meaningful signal-to-noise ratio, permitting the ready analysis of reaction products without resort to time consuming molecular weight-based separation steps such as, e.g., gel electrophoresis, capillary zone electrophoresis, size exclusion chromatography or mass spectroscopy, or other types of chromatography such as, e.g., paper chromatography or reverse-phase column chromatography.

The methods of the invention permit rapid analysis of many proteins and many of the steps are easily automated. A rapid, automated screening method dramatically reduces the cost of analyzing protein expression and is readily implemented using standard parallel processing in 96 well, 384 well and other standard microtiter plate formats. The methods are readily applicable to analysis of large cDNA collections such as the LLNL IMAGE collection.

Kits of the Invention

Kits of the invention preferably include reagents for practicing the methods of the invention, containers for carrying out reactions, substrates for spotting the reaction products, instructions for use, and packaging. Reagents may include wash buffers, PCR reaction mixtures, enzymes, and labels (including direct and indirect labels such as labeled amino acyl tRNAs, preferably fluorescently labeled on the amino acyl moiety, and antibody reagents for labeling tagged in vitro translation products). The kit optionally may comprise a subset of the above-listed components, but preferably includes at least reagents for in vitro translation, labels, wash buffers, and instructions.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for. Unless otherwise indicated, all procedures and steps are carried out at room temperature (i.e., from about 20° C. to about 25° C.).

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W. H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences*, 18th Edition (Easton, Pa.: Mack Publishing Company, 1990); Carey and Sundberg *Advanced Organic Chemistry* $3^{rd}$ Ed. (Plenum Press) Vols A and B(1992).

Example 1

IVT Expression Screening Protocol (96-Well Format)

PCR Amplification

A master mix for 100 reactions is made containing all reagents except for the DNA template and is transferred to a 96-well plate using a multichannel pipette. The following assumes that DNA template is in a 1 μL volume.

PCR Master Mix (Volume Per Reaction)

```
Taq 10x Buffer              5 µL dNTPs (2 mM each)           1 µL

Primers (10 µM)             1 µL each (T7 promoter and terminator clamp
primers, respectively:)

(SEQ ID NO: 1)
[5'-GTCGCGCGAGATCTCGATCCCGCGAAATTAATACGAC
and (SEQ ID NO: 2)
5'-GCGCGCGTATCCGGATATAGTTCCTCCTTTCAG Taq DNA Pol. (5 U/µL)       0.25 µL (Roche 11418432001)

Sterile H₂O to total volume of 49 µL
```

In a PCR compatible 96-well plate, e.g. Costar Thermowell (Coming 6551), combine 49 μL of the PCR Master Mix with 1 μL (1-10 ng) plasmid template (containing T7 promoter/ terminator). The plate is sealed with Amplification Tape (Nalge Nunc 232702).

Amplification conditions (using MJ Research PTC-200 Thermal Cycler):
1. 94° C. 2.5 min
2. 94° C. 1 min
3. 50° C. 1 min
4. 72° C. 2 min (or 1 min per kb for largest gene)
5. Repeat steps 2-4, 30 times
6. 72° C. 10 min
7. 4° C. hold Run analytical agarose gel using 5 μL of PCR sample (or detect by rapid, alternate method such as PicoGreen dsDNA Quantitation Kit (Molecular Probes P-7589).

Precipitate DNA with 2 volumes of 100% EtOH, 0.1 volume 3 M NaOAc and incubate at −70° C. for 30 min. Centrifuge 10 min in Eppendorf centrifuge with plate rotor, 4,000 rpm (3,250×g). Wash pellet (do not vortex) with 100 μL of 70% EtOH and centrifuge again for 5 min. Air-dry the pellets and resuspend DNA in 15 μL of water.

In an alternate embodiment, PCR reaction products are prepared and used in the IVT reaction without prior purification.

IVT Reaction

The first five reagents of the IVT Master Mix are provided in the RTS-100 kit (Roche 3186148 or 3186156), and are reconstituted according to the manufacturer's protocols.

| IVT Master Mix (volume per reaction) | | |
|---|---|---|
| Lysate | 6 μL | |
| Reaction Mix | 5 μL | |
| Amino Acids Mix | 6 μL | |
| Methionine | 0.5 μL | |
| Reconstitution Buffer | 2.5 μL | |
| Fluorotect GreenLys | 0.4 μL | (Promega L5001) |

20.4 μL of IVT Master Mix are combined with 4.6 μL of DNA template in a PCR compatible 96-well plate, which is then sealed with Amplification Tape and incubated at 30° C. 4 h to overnight in a thermal cycler.

Note that IVT reactions also may be carried out in a reaction volume ½ or less of that described. Approximately sixty 25 μL reactions can be performed using a 24 reaction kit. Good results are obtained with 0.25 to 0.5 μL of FluoroTect per 25 μL IVT reaction.

Plasmid DNA may also be used as the template for IVT reactions. Non-T7 based gene clones are PCR amplified to contain the proper T7 regulatory sequences using the Linear Template Generation Set (Roche 03186237001).

Spotting Using a Dot-Blot Apparatus

For analysis of soluble vs. insoluble protein, 10 μL of the IVT products are diluted 1:20 in Urea Lysis Buffer [8 M urea, 20 mM Tris-HCl, 10 mM NaPO4, pH 8.0] in a new microplate. The remaining IVT products are fractionated by centrifugation in a microplate rotor at 4,000 rpm (3,250×g) for 10 min. 10 μL of the soluble (supernatant) fraction are removed and diluted 1:20 as above.

Total and soluble protein fractions are applied to an Immobilon-P PVDF membrane (Millipore IPVH15150) using a Bio-Dot vacuum blotting apparatus (Bio-Rad 1703938). In most applications approximately 5 μL to 10 μL of reaction volume is spotted. The membrane is washed three times using volumes and vacuum pressures recommended by the manufacturer, i.e., wash volumes ~100 mL each using house vacuum pressure, once with Urea Lysis Buffer and twice with 1×PBS [80 mM NaPO4, 20 mM NaPO4, 100 mM NaCl, pH 7.5] to remove unincorporated BODIPY-Lys-tRNA$_{Lys}$. The apparatus is disassembled and the membrane is further washed in ~50 mL of 1×PBST [PBS containing 0.1% (v/v) Tween-20] for 30 min.

Fluorescence Detection

The fluorescence signal is acquired on a FluorImager 595 flatbed fluorescence scanner (Molecular Dynamics) using a 488 nm excitation filter, high sensitivity and high resolution settings. The fluorescence signal is quantified with the volume report feature provided in ImageQuant software (Molecular Dynamics). Data are exported to Microsoft Excel for background subtraction and display.

The detection step may be performed with standard fluorescence plate readers (e.g. Tecan Genios) if filter plates (e.g. Pall Acrowell Filterplate 5022) are used in place of the dot-blot apparatus.

Other Detection Methods

Expressed proteins are detected by a dot-blot procedure as described above (using, e.g., 5 µl IVT reaction) using an Immobilon-P membrane (Millipore) or by SDS-PAGE (6 µl, acetone-precipitated IVT reaction) or by immunoblot using a Penta-His 1° antibody (Ab) (1:1000) (Qiagen) and an HRP-conjugated anti-mouse 2° Ab (Amersham). Gels and blots are visualized on a FluorImager 595 (Molecular Devices).

Example 2

Protein Microarrays

To analyze protein interactions, IVT-expressed proteins, purified proteins and antibodies (1-10 mg/ml) were spotted in duplicate on CMT-GAPS glass slides (Corning) with a robotic arrayer (Norgren Systems). Arrays contained up to 224 spots (~200 µm diameter). Controls included proteins (BSA, His6-GFP, Ape1) and nucleic acids [M13 ssDNA, M13 dsDNA, 20-mer oligos, RNA, Cy-labeled DNA fragments (Molecular Probes)]. The arrays were dried at 25° C. and stored at 4° C. until use. Fluorescence was quantified using a ScanArray 5000 (Packard Bioscience) and visualized with false color.

For far-Western experiments, arrays were incubated with 25-50 ng of a purified protein (15 min, 25° C.) and washed with phosphate-buffered saline (PBS) or PBS+0.1% Tween-20 (PBST). Interactions were detected with a primary antibody (RAD51 paralog- or SMARCAL1-specific Ab) (1:500), which was incubated (30 min, 25° C.) and washed with PBST. Rhodamine-labeled secondary Ab (1:250) was then added (15 min, 25° C.) and slides were washed and imaged as above.

Example 3

Results

Choice of Expression System

Cell-free protein expression in an *E. coli* extract was used because of its relatively high yield, its suitability for high-throughput automation and the potential to scale up reaction volumes (1-10 ml). Extracts from several suppliers were tested and RTS extracts (Roche) demonstrated favorable expression yields (data not shown). Using RTS extracts, efficient, cell-free expression from plasmid and PCR-amplified DNA templates were performed.

To test the ability of IVT screening to predict bacterial expression levels, the correlation of IVT- and *E. coli*-expressed proteins using 13 different human and bacterial clones, expressed as C-terminal green fluorescent protein (GFP) fusions [10], were examined. The expression data cluster into two groups; the eight most highly expressed clones exhibit a good correlation (cc=0.89), whereas the five least highly expressed clones display a weaker correlation (overall cc=0.69). The in vitro expression levels of the latter five clones were significantly higher than the in vivo levels. Therefore, this set may comprise proteins that are cytotoxic or proteolytically sensitive, which underscores the benefits of cell-free expression for certain classes of proteins.

High-Throughput, Cell-Free Protein Expression

One useful application of high-throughput, cell-free protein expression is the identification of expressed proteins from hypothetical genes or cDNA expression libraries, which has previously been done in vivo [11]. The RTS system has been applied to high-throughput protein expression to identify highly expressed proteins for structural studies. This approach indicates which clones are candidates for larger RTS reactions that employ continuous nutrient exchange [12, 13] to achieve yields of up to ~5 mg protein ml extract, or in bacterial expression systems.

The screening strategy consists of several steps, including: (1) PCR amplification of target genes; (2) cell-free protein expression using RTS 100, with optional incorporation of a fluorescent label or affinity tag; (3) transfer to membrane; and (4) detection by fluorescence or immunoblotting (see above Methods). Using fluorescence detection, the entire procedure can be carried out in approximately 7 hours. For non-T7 based clones, an extra PCR amplification step can be performed to incorporate the necessary regulatory sequences (Linear Template Generation Set, Roche).

Protein Expression Screening

IVT expression testing was performed on 48 different clones, including prokaryotic and eukaryotic clones and several different expression plasmids, pIVEX2.4b (Roche), pET28 and pETBlue (Novagen). The blot was visualized by BODIPY fluorescence (FIG. 1A) and the spot intensities were quantified (FIG. 1B). FIG. 1A is a BODIPY-labeled dot-blot of 48 clones, in duplicate (rows A through H, columns 1-6 and 7-12), imaged with a FluorImager 595 (Molecular Devices). Twofold serial dilutions of a HIS6-GFP control reaction are shown in the top strip. FIG. 1B is quantification reported as relative fluorescence units (RFU) from the blot shown in FIG. 1A (rows A-H, columns 1-12). This results demonstrate that the BODIPY-Lys conjugate is efficiently incorporated, that there is wide variation among different constructs and that duplicate reactions are comparable. An immunoblot of the same membrane (rows A-H, columns 1-12)using an affinity tag-specific antibody (FIG. 1C) offers the advantages that the signal does not depend on the number of lysine residues in the protein and that the quantities can be more easily standardized. FIG. 1C is an immunoblot of the same membrane shown in FIG. 1A but using a penta-His antibody (Qiagen). Only a subset of the clones encoded a His6 tag (SEQ ID NO: 3). In addition, proteins without BODIPY-conjugated lysine residues are more likely to retain their native functional properties. However, His6 tags (SEQ ID NO: 3) are also known to have effects on protein solubility and enzyme activity for some proteins [14]. The immunoblot (FIG. 1C) identifies some of the same clones as the BODIPY-based detection (A1, B1, C1, E1), but does not identify the clones lacking a His6 tag (SEQ ID NO: 3)(A3, B3, G2). Truncated proteins arising from premature translational termination are not detected in immunoblots of C-terminal His6 tagged (SEQ ID NO: 3) proteins. According to the methods of the invention, labeling the in vitro translated reaction product can be accomplished using direct labeling and indirect labeling, indirect labeling indicating labeling by a secondary antibody harboring a label. FIG. 1D is an image of an SDS PAGE of selected reactions from the same experiment. Lane 1 shows mass standards (at left, kDa); lane 2 is purified GFP (3 µg); lane 3 A7 (pIVEX-GFP); lane 4 A8 (no DNA template); lane 5 B7; lane 6 is C7; lane 7 is G8; lane 8 is A9; lane 9 is B9.

Protein Microarrays

Figure 2:
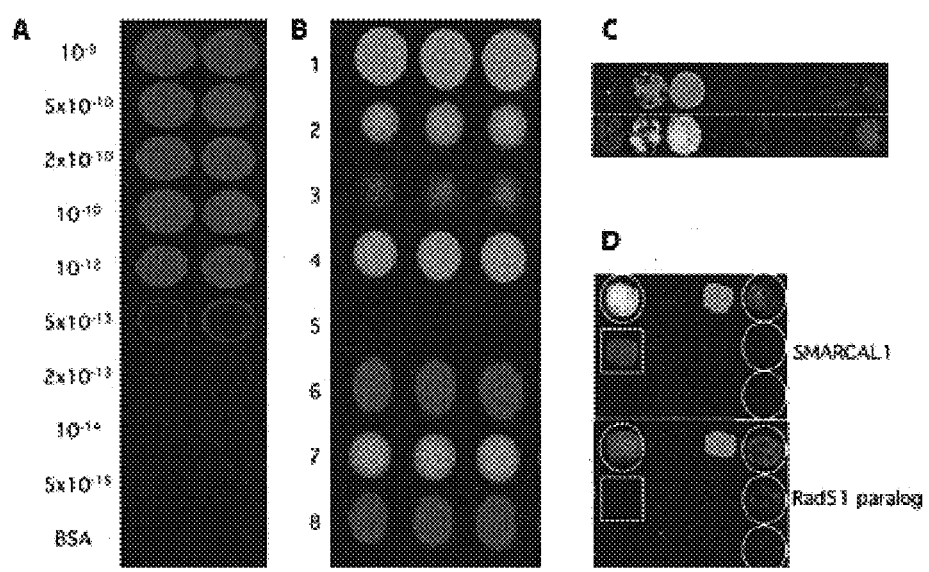
FIG. 2 depicts various microarray-based protein visualization and interaction analyses on glass slides.

IVT-expressed proteins were spotted on microarrays for several applications. First, for expression screening, arrays for comparison of relative expression levels were used. Control experiments were conducted to identify the limit of fluorescence detection by arraying purified GFP on a glass slide (CMT-GAPS, Corning) (FIG. 2A). The limit of detection using the experimental configuration was determined to be on the order of approximately ($2 \times 10^{-13}$ g). IVT-expressed GFP fusion proteins also were arrayed, which showed that spotting was reproducible and therefore useful to identify differences in relative expression levels (FIG. 2B). FIG. 2B shows DNA (red) and IVT-expressed proteins (green) arrayed on a glass slide to assess spotting reproducibility. Row: 1 LcrH; 2 GFP; 3 XRCC1; 4 LcrG; 5 IVT extract; 6 DNA; 7 SFN5; 8 DNA.

Second, for protein-specific detection, array-based immunoassays to detect GFP fusion proteins (FIG. 2C) were performed. Top row of FIG. 2C shows the fluorescence of IVT-produced GFP fusions. The bottom row shows GFP fusion protein detection using an anti-GFP primary antibody (BD Clontech) and a rhodamine-conjugated secondary antibody. These experiments can be adapted for protein expression profiling studies using cellular extracts.

Biochemical Assays

It is important for subsequent biochemical studies that IVT-expressed proteins be functionally active. IVT-expressed proteins have been used to measure enzymatic activities and interactions. IVT- and bacterially expressed Ape1 enzymes were similar in DNA-binding and structure-specific nuclease activities (data not shown). For detection of protein interactions, an array-based far-Western technique was developed. To investigate the interactions of putatively interacting proteins, a microarray was constructed that included nucleic acids, histones and nucleosomes. This array was used in far-Western experiments to identify interactions of SMARCAL1 [15] with nucleosomes and a Rad51 paralog with individual histones. IVT-expressed SMARCAL1 interacted with nucleosomes and not with individual histones H1, H2A, H2B and H4 (FIG. 2D). Also SMARCAL1-nucleosomal interactions were modulated in the presence of ATP. These results help to define the functional interactions of SMARCAL1. These and similar experiments demonstrate that proteins can be expressed in vitro and assayed directly for biochemical functions and interactions without purification.

FIG. 2D illustrates protein interactions demonstrated on an array containing 224 duplicate spots (only a portion of the array is shown in the Figure). SMARCAL1 associates primarily with nucleosomes (squares) and only weakly with individual histones (circles). In addition, a RAD51-paralog has affinity for free histones (circles) but not nucleosomes (squares).

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. Pedelacq J D, Piltch E, Liong E C, Berendzen J, Kim C Y, Rho B S, Park M S, Terwilliger T C, Waldo G S (2002) Engineering soluble proteins for structural genomics. Nat Biotechnol 20: 927-932
2. Yokoyama S (2003) Protein expression systems for structural genomics and proteomics. Curr Opin Chem Biol 7: 39-43
3. Fields S, Song O (1989) A novel genetic system to detect protein interaction. Nature 340: 245-246
4. Schweitzer B, Kingsmore S F (2002) Measuring proteins on microarrays. Curr Opin Biotechnol 13: 14-19
5. Pawlak M, Schick E, Bopp M A, Schneider M J, Oroszlan P, Ehrat M (2002) Zeptosens' protein microarrays: a novel high-performance microarray platform for low abundance protein analysis. Proteomics 2: 383-393
6. Haab B B, Dunham M J, Brown P O (2001) Protein microarrays for highly parallel detection and quantitation of specific proteins and antibodies in complex solutions. Genome Biol 2:research0004.1-0004.13
7. Kononen J, Bubrndorf L, Kallioniemi A et al. (1998) Tissue microarrays for high throughput molecular profiling of tumor specimens. Nature Medicine 4: 844-847
8. Huang R P (2001) Detection of multiple proteins in an antibody-based protein microarray system. J Immunol Methods 255: 1-13
9. Wiese R, Belosludtsev Y, Powdrill T, Thompson P, Hogan M (2001) Simultaneous multianalyte ELISA performed on a microarray platform. Clinical Chem 47: 1451-1457
10. Waldo G S, Standish B M, Berendzen J, Terwilliger T C (1999) Rapid protein-folding assay using green fluorescent protein. Nat Biotechnol 17: 691-695
11. Bussow K, Nordhoff E, Lubbert C, Lehrach H, Walter G (2000) A human cDNA library for high-throughput protein expression screening. Genomics 65: 1-8
12. Spirin A S (1992) Gene expression in cell-free systems on a preparative scale. Bioorg Khim 18: 1394-1402
13. Martin G A, Kawaguchi R., Lam Y, DeGiovanni A, Fukushima M, Mutter W (2001) High-yield, in vitro protein expression using a continuous-exchange, coupled transcription/translation system. BioTechniques 31: 948-953
14. Hammarstrom M, Hellgren N, van Den Berg S, Berglund H, Hard T (2002) Rapid screening for improved solubility of small human proteins produced as fusion proteins in *Escherichia coli*. Protein Sci 11: 313-321
15. Coleman M A, Eisen J A, Mohrenweiser H W (2000) Cloning and characterization of HARP/SMARCAL1: a prokaryotic HepA-related SNF2 helicase protein from human and mouse. Genomics 65: 274-282
16. Doyle S A, Murphy M B, Massi J M, Richardson P M (2002) High-throughput proteomics: a flexible and efficient pipeline for protein production. J Proteome Res 1: 531-53

What is claimed is:

1. A method for parallel analysis of a plurality of in vitro transcription/translation reactions, said method comprising:

carrying out said plurality of in vitro transcription/translation reactions in a plurality of reaction mixtures in wells of a multiwell plate to generate a plurality of reaction products, wherein each non-control reaction mixture comprises cell-free protein expression reagents and at least one nucleic acid template;

spotting said plurality of reaction mixtures including reaction products onto a substrate wherein the substrate is optionally coated, wherein said reaction products bind directly to said substrate or said coated substrate, wherein said substrate comprises a membrane or a glass slide and wherein said spotting is carried out without use of a separation step that provides information about molecular weights of reaction products and without an intervening purification step; and detecting said plurality of in vitro transcription/translation reaction products bound to said substrate.

2. The method of claim 1, wherein said substrate is said membrane.

3. The method of claim 2, wherein said membrane comprises PVDF.

4. The method of claim 1, wherein said substrate is said glass slide.

5. The method of claim 1, wherein said coated substrate is a coated glass slide.

6. The method of claim 5, wherein said coating comprises poly-L-lysine.

7. The methods of claim 1, wherein said detecting step comprises use of an antibody.

8. The method of claim 7, wherein said antibody includes an enhanced chemiluminescent label.

9. The method of claim 1, further comprising carrying out said plurality of in vitro transcription/translation reactions in the presence of a labeled aminoacyl tRNA, said labeled amino acyl tRNA comprising a label on the amino acid moiety of said amino acyl tRNA to generate said plurality of in vitro transcription/translation reaction products that are labeled.

10. The method of claim 9, wherein said label is a fluorescent label.

11. The method of claim 1, wherein said plurality of in vitro transcription/translation reactions comprises at least 13 reactions.

12. The method of claim 1, wherein said plurality of in vitro transcription/translation reactions comprises at least 48 reactions.

13. The method of claim 1, wherein said plurality of in vitro transcription/translation reactions comprises at least 96 reactions.

14. The method of claim 1, wherein said plurality of in vitro transcription/translation reactions comprises at least 224 reactions.

15. The method of claim 1, wherein said plurality of in vitro transcription/translation reactions comprises at least 384 reactions.

16. The method of claim 1, wherein said cell-free expression reagents comprise an E. coli lysate and said nucleic acid template comprises DNA.

17. The method of claim 1, further comprising amplifying a plurality of nucleic acid samples to generate the nucleic acid templates prior to the step of carrying out a plurality of in vitro transcription/translation reactions.

* * * * *